United States Patent
Kojima et al.

(10) Patent No.: US 9,662,136 B2
(45) Date of Patent: May 30, 2017

(54) CELLULAR TISSUE DISSECTION METHOD AND LIQUID EJECTION DEVICE

(71) Applicant: SEIKO EPSON CORPORATION, Tokyo (JP)

(72) Inventors: Hideki Kojima, Matsumoto (JP); Toshiki Endo, Sendai (JP); Atsuhiro Nakagawa, Sendai (JP); Tominaga Teiji, Sendai (JP)

(73) Assignee: SEIKO EPSON CORPORATION, Tokyo (JP)

( * ) Notice: Subject to any disclaimer, the term of this patent is extended or adjusted under 35 U.S.C. 154(b) by 161 days.

(21) Appl. No.: 14/736,198

(22) Filed: Jun. 10, 2015

(65) Prior Publication Data
US 2015/0359555 A1    Dec. 17, 2015

(30) Foreign Application Priority Data
Jun. 11, 2014    (JP) .................... 2014-120268

(51) Int. Cl.
*A61B 17/32*    (2006.01)
*A61B 17/3203*    (2006.01)
*A61B 17/00*    (2006.01)

(52) U.S. Cl.
CPC    *A61B 17/3203* (2013.01); *A61B 2017/00154* (2013.01)

(58) Field of Classification Search
CPC ............... A61B 17/3203; A61B 2017/00154
See application file for complete search history.

(56) References Cited

U.S. PATENT DOCUMENTS

| | | | | |
|---|---|---|---|---|
| 2006/0229550 | A1* | 10/2006 | Staid | A61B 17/3203 604/27 |
| 2008/0086077 | A1 | 4/2008 | Seto et al. | |
| 2010/0082053 | A1* | 4/2010 | Hama | A61B 17/3203 606/167 |

FOREIGN PATENT DOCUMENTS

JP    2008-082202 A    10/2008

* cited by examiner

*Primary Examiner* — Todd J Scherbel
*Assistant Examiner* — Son Dang
(74) *Attorney, Agent, or Firm* — Maschoff Brennan

(57) ABSTRACT

An incision is formed at a site where a cellular tissue is to be dissected. A liquid is ejected to the incision. The incision is expanded. The cellular tissue is dissected. The liquid is ejected in the form of a pulse flow. The liquid is ejected in such a way as to advance obliquely to a tangential direction to a surface of the cellular tissue. A site where the liquid is applied to the surface is moved in a direction in which an angle formed by the surface and the direction of advancement of the liquid is greater.

3 Claims, 6 Drawing Sheets

CELLULAR TISSUE DISSECTION METHOD AND LIQUID EJECTION DEVICE

This application claims the benefit of Japanese Patent Application No. 2014-120268, filed on Jun. 11, 2014. The content of the aforementioned application is incorporated herein by reference in its entirety.

BACKGROUND

1. Technical Field

The present invention relates to a cellular tissue dissection method and a liquid ejection device.

2. Related Art

Dissection processing is broadly employed in which a cellular tissue in a muscle, organ, tunic, blood vessel, tumor or the like is separated, severed and thus excised or stripped off. In this processing, a metallic surgical knife, electric surgical knife, laser surgical knife, water jet surgical knife or the like is used.

The water jet surgical knife dissects a cellular tissue with the impact energy of a water jet flow. The water jet surgical knife is able to dissect only the tissue without damaging any nerves, blood vessels or the like. JP-A-2008-82202 discloses a liquid ejection device as a water jet surgical knife. According to this, the liquid ejection device has a pulsation generator which applies pulsation to a fluid. The pulsating fluid is ejected to a cellular tissue, thus dissecting the cellular tissue.

If the connection between cells of a cellular tissue is strong, the cellular tissue is not separated unless a high-pressure pulse flow is ejected. With the high-pressure ejection, the surface of the tissue is separated and subsequently the high-pressure pulse flow is ejected into the cellular tissue. This may cause the tissue to be separated to a greater depth than the planned depth. Thus, there is a demand for a cellular tissue dissection method that can easily control the depth and direction in which a cellular tissue is dissected.

SUMMARY

An advantage of some aspects of the invention is to solve at least a part of the problems described above, and the invention can be implemented as the following forms or application examples.

Application Example 1

This application example is directed to a cellular tissue dissection method including: forming an incision at a site where a cellular tissue is to be dissected; and ejecting a liquid to the incision, expanding the incision, and dissecting the cellular tissue.

According to this application example, the incision is formed at the site where the cellular tissue is to be dissected. Then, the liquid is ejected to the incision, thus expanding the incision. The cellular tissue is dissected by the water pressure of the ejected liquid. When the liquid is ejected to the incision, stress concentrates at the end of the incision. Therefore, even when the water pressure is low, the cellular tissue can be dissected easily.

An extremely high water pressure is needed when there is no incision. The water pressure at the time of dissecting the surface of the cellular tissue reaches the insides of the cellular tissue. Since the extremely high water pressure is applied to the inside of the cellular tissue, it is difficult to control the depth to which the cellular tissue is dissected.

Meanwhile, when the liquid is ejected to the incision, the dissection can be achieved with a lower water pressure and therefore the water pressure can be prevented from reaching deep parts of the cellular tissue. Also, since the incision is formed, dissection in an unintended direction can be avoided. Therefore, the depth to which the cellular tissue is dissected can be controlled easily.

Application Example 2

In the cellular tissue dissection method according to the application example described above, the liquid may be ejected in the form of a pulse flow.

According to this application example, the liquid is ejected in the form of a pulse flow. With the pulse flow, the pressure fluctuation applied to the cellular tissue can be made greater, compared with a continuous flow. As the pressure fluctuation increases, fatigue fracture can occur more easily in the part connecting cells together. Therefore, the cellular tissue can be dissected easily.

Application Example 3

In the cellular tissue dissection method according to the application example described above, the liquid may be ejected in such a way as to advance obliquely to a tangential direction to a surface of the cellular tissue. A site where the liquid is applied to the surface may be moved in a direction in which an angle formed by the tangential direction to the surface and the direction of advancement of the liquid is greater.

According to this application example, the liquid is ejected in such a way as to advance obliquely to the tangential direction to the surface of the cellular tissue. The liquid accumulates in the incision at the site where the liquid is ejected. Then, the site where the liquid is applied to the surface is moved in the direction in which the angle formed by the surface and the direction of advancement of the liquid is greater. Therefore, the ejection of the liquid is moved in such a way as to push the liquid accumulating in the incision. Consequently, the liquid pushed by the water pressure heads in the direction of pressing and expanding the incision. Therefore, the incision can be expanded easily.

Application Example 4

This application example is directed to a liquid ejection device including: a nozzle which ejects a liquid; and an edge portion.

According to this application example, the liquid ejection device has the nozzle for ejecting the liquid and the edge portion. The surgical operator can form an incision on the surface of a cellular tissue, using the edge portion, and then eject the liquid from the nozzle toward the incision. Thus, since dissection can be achieved with a low water pressure along the incision at the time of forming the incision, the depth and direction in which the cellular tissue is dissected can be easily controlled. Since the liquid ejection device has the edge portion, the surgical operator can carry out the formation of the incision and the ejection of the liquid, using the liquid ejection device. Thus, the surgical operator need not hold the knife first and then the liquid ejection device. Therefore, the cellular tissue can be dissected with high operability.

Application Example 5

In the liquid ejection device according to the application example described above, the edge portion may be installed side by side with the nozzle. An end of the edge portion may be installed, protruding ahead of an end of the nozzle in a direction in which the liquid is ejected.

According to this application example, the edge portion is installed side by side with the nozzle. The end of the edge portion is installed, protruding ahead of the end of the nozzle in the direction in which the liquid is ejected. Therefore, the surgical operator can carry out the formation of the incision and the ejection of the liquid without changing the way of holding the liquid ejection device.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1A:
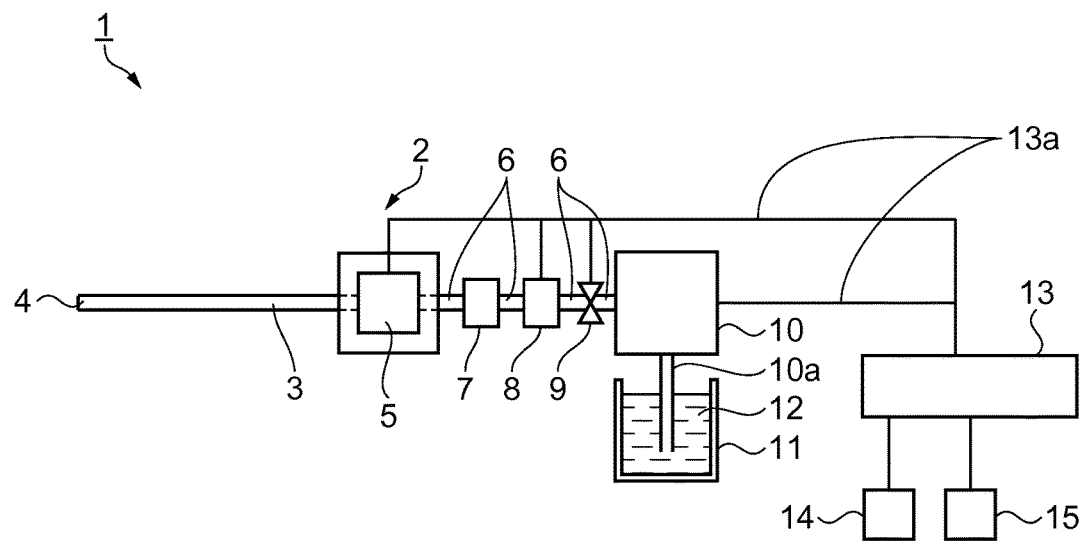
FIG. 1A is a block diagram showing the configuration of a liquid ejection device according to a first embodiment.

In the embodiments, a characteristic liquid ejection device and a characteristic example of a method for dissecting a cellular tissue using this liquid ejection device will be described with reference to the drawings. Hereinafter, the embodiments will be described with reference to the drawings. Each member in the drawings is illustrated not to scale, in order to show the member in a recognizable size in each drawing.

First Embodiment

Figures 1B, 1C:
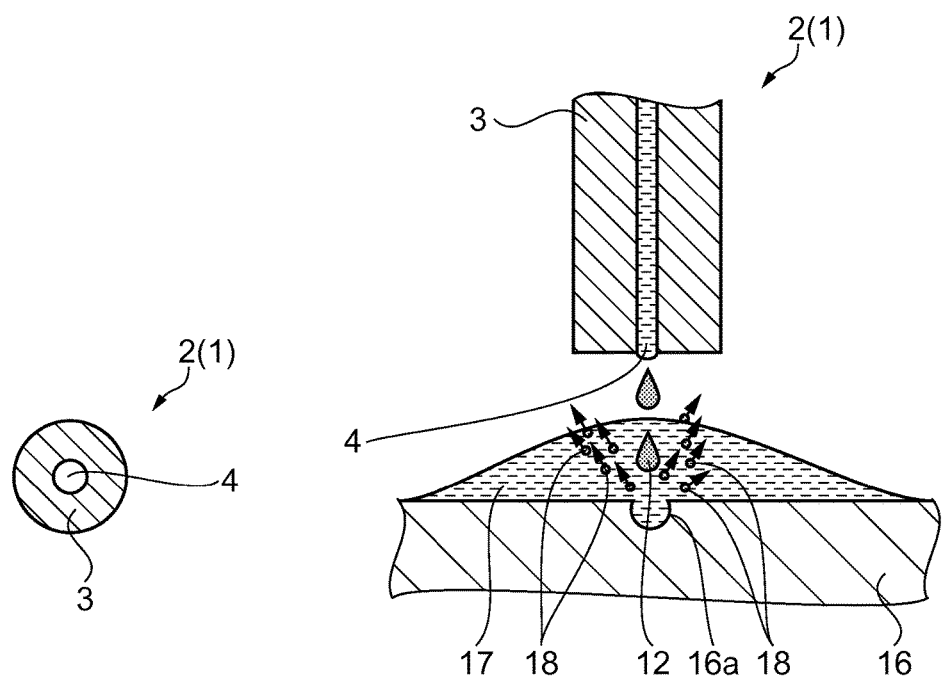
FIG. 1B is a partial schematic side view showing the structure of a nozzle in the liquid ejection device.
FIG. 1C is a schematic view for explaining the behavior of a liquid in the nozzle.

In this embodiment, a liquid ejection device as a surgical apparatus will be described with reference to FIGS. 1A to 5D. FIG. 1A is a block diagram showing the configuration of the liquid ejection device. FIG. 1B is partial schematic side view showing the structure of a nozzle in the liquid ejection device. The liquid ejection device 1 of this embodiment is a medical apparatus used in a medical institution and has the function of a surgical knife which ejects a fluid to an affected part and thus incises or excises the affected part. The liquid ejection device 1 can also be used for treatment and autopsy of other animals than humans.

As shown in FIG. 1A, the liquid ejection device 1 has a handpiece 2. The handpiece 2 is a device which the surgical operator holds in his/her hand and operates when carrying out a surgical operation. In other situations than surgical operation, the surgical operator is also referred to as an operator. An ejection tube 3 that is a channel for a fluid is installed in the handpiece 2. At one end of the ejection tube 3, a nozzle 4 as a liquid ejection opening for ejecting a fluid is installed. At the other end of the ejection tube 3, a pulsation applying part 5 is installed. A filter 7, a flowmeter 8, a solenoid valve 9, and a pump 10 are connected to the pulsation applying part 5 in this order via a tube 6. The pulsation applying part 5 is apart where the fluid passing through this part is turned into a pulse flow.

The filter 7 has the function of eliminating foreign matters, bacteria, air bubbles and the like contained in the fluid. The flowmeter 8 measures the flow rate of the fluid flowing through the tube 6. As the flowmeter 8, a hot-wire flowmeter, impeller flowmeter or the like can be used. The solenoid valve 9 is a valve controlled to open and close by an electrical signal. As the solenoid valve 9, a valve that opens and closes by a motor or electromagnet can be used.

As the pump 10, a syringe pump or tube pump can be used. In the case of a syringe pump, it is preferable that a device for supplying a fluid into the syringe is installed. This enables the liquid ejection device 1 to be driven continuously.

An inlet tube 10a is installed in the pump 10. One end of the inlet tube 10a is connected with a reservoir 11. There is a liquid 12 in the reservoir 11. As the liquid 12, for example, a physiological saline solution is used. The physiological saline solution is harmless to a living body and therefore can be used for a surgical operation.

The liquid ejection device 1 has a control device 13 as a control unit. The control device 13 controls the operations of the liquid ejection device 1. The pulsation applying part 5, the flowmeter 8, the solenoid valve 9 and the pump 10 are connected with the control device 13 via a cable 13a.

A main switch 14, an ejection switch 15 as a switch, and the like are installed on the control device 13. The main switch 14 is a switch for starting up the liquid ejection device 1. As the main switch 14 is turned on, electric power is supplied to the control device 13. The ejection switch 15 is a switch for switching between ejection and non-ejection of a fluid from the nozzle 4. The ejection switch 15 is a switch which the surgical operator steps on to operate.

As the surgical operator turns on the main switch 14, initial setting of the control device 13 is carried out. Then, the surgical operator turns on the ejection switch 15. The pump 10 is thus started up. The pump 10 causes the fluid 12 to flow to the solenoid valve 9. As the control device 13 opens the solenoid valve 9, the high-pressure liquid 12 in the form of a fluid advances into the tube 6. Then, the flowmeter 8 detects the flow rate of the fluid advancing through the tube 6 and outputs the detected flow rate to the control device 13.

The fluid advancing through the tube 6 passes through the filter 7. The filter 7 eliminates dust, air bubbles, salt crystals and the like from the liquid 12. To the liquid 12 reaching the pulsation applying part 5, pulse-like pulsation is applied by the pulsation applying part 5. A pulse-like pulsed flow is referred to as a pulse flow. The liquid 12 passing through the pulsation applying part 5 then passes through the ejection tube 3 and is ejected from the nozzle 4. The liquid 12 passing through the nozzle 4 is a pulse flow and therefore is ejected in the form of a pulse flow. As shown in FIG. 1B, the ejection tube 3 is a tube with the nozzle 4 located in the center. The liquid 12 in the form of a pulse flow is ejected from the nozzle 4.

FIG. 1C is a schematic view for explaining the behavior of the liquid in the nozzle. As shown in FIG. 1C, the surgical operator operates the handpiece 2 to move the nozzle 4 toward a cellular tissue 16. As the surgical operator turns on the ejection switch 15, the liquid 12 is ejected from the nozzle 4 and the liquid 12 collides with a collision point 16a on the cellular tissue 16. A liquid pool 17 of the accumulating liquid 12 is formed around the collision point 16a. Then, a cell group 18 in a part of the cellular tissue 16 is separated from the cellular tissue 16.

Figure 2A:
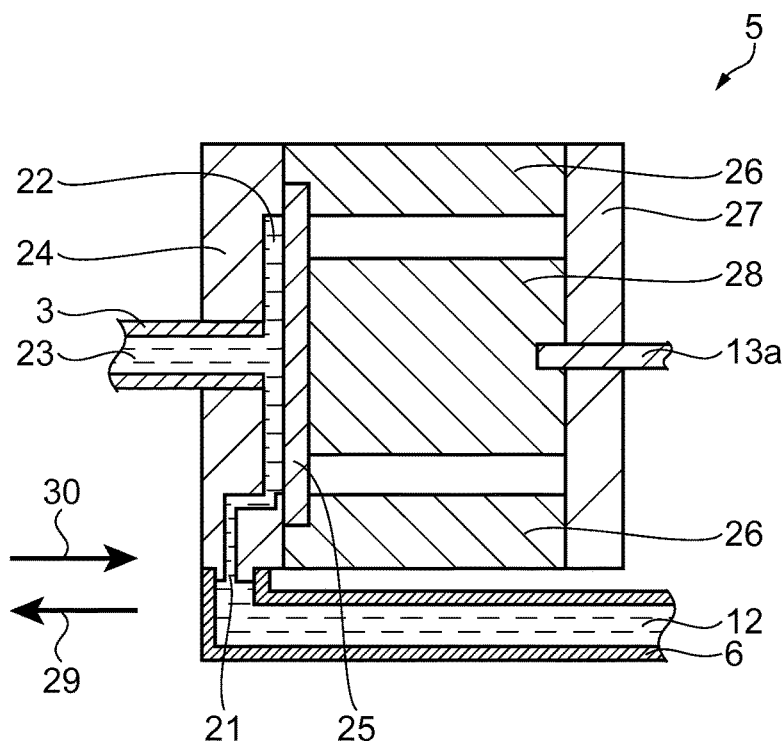
FIG. 2A is a schematic cross-sectional view showing the internal configuration of a pulsation applying part.

FIG. 2A is a schematic cross-sectional view showing the internal configuration of the pulsation applying part. In the pulsation applying part 5, an inlet channel 21, a liquid chamber 22 and an outlet channel 23 through which the liquid 12 supplied from the tube 6 passes are installed. The inlet channel 21 and the outlet channel 23 are formed in a first case 24. A diaphragm 25 is installed in such a way as to hold the liquid chamber 22 between the first case 24 and the diaphragm 25. The tube 6 is connected with the inlet channel 21. The ejection tube 3 is connected with the outlet channel 23.

On the right-hand side of the first case 24 in the illustration, a cylindrical second case 26 is installed in contact with the first case 24. The diaphragm 25 is a disk-shaped thin metal plate. An outer peripheral part of the diaphragm 25 is held and fixed between the first case 24 and the second case 26. On the right-hand side of the second case 26 in the illustration, a third case 27 is installed in contact with the second case 26. A piezoelectric element 28 as a volume varying unit, which is a multilayer piezoelectric element, is arranged between the diaphragm 25 and the third case 27. One end of the piezoelectric element 28 is fixed to the diaphragm 25. The other end thereof is fixed to the third case 27. The piezoelectric element 28 is connected with the control device 13 via the cable 13a.

As a drive voltage is applied from the control device 13, the piezoelectric element 28 changes the volume of the liquid chamber 22 formed between the diaphragm 25 and the first case 24. As the drive voltage applied to the piezoelectric element 28 rises, the piezoelectric element 28 expands, and the diaphragm 25 is pressed by the piezoelectric element 28 and thus flexes toward the liquid chamber 22, that is, in a first direction 29 in the illustration. As the diaphragm 25 flexes in the first direction 29, the volume of the liquid chamber 22 decreases. Then, the fluid inside the liquid chamber 22 is pushed out of the liquid chamber 22. The inner diameter of the outlet channel 23 is greater than the inner diameter of the inlet channel 21. That is, the fluid resistance in the outlet channel 23 is lower than the fluid resistance in the inlet channel 21. Since the inlet channel 21 is closer to the pump 10 than the outlet channel 23, the water pressure in the inlet channel 21 is higher than the water pressure in the outlet channel 23. Therefore, the major part of the fluid inside the liquid chamber 22 is pushed out of the liquid chamber 22 through the outlet channel 23.

Meanwhile, as the drive voltage applied to the piezoelectric element 28 falls, the piezoelectric element 28 contracts, and the diaphragm 25 is pulled by the piezoelectric element 28 and thus flexes toward the third case 27, that is, in a second direction 30 in the illustration. The piezoelectric element 28 contracts and the volume of the liquid chamber 22 increases. Therefore, the fluid is supplied into the liquid chamber 22 from the inlet channel 21.

The drive voltage applied to the piezoelectric element 28 repeats on-state (maximum voltage) and off-state (0 V) at a high frequency (for example, 300 Hz). Therefore, expansion and contraction of the volume of the liquid chamber 22 are repeated, thus applying pulsation to the fluid. The fluid pushed out of the liquid chamber 22 is ejected in the form of a pulse flow from the nozzle 4 at the end of the ejection tube 3. The ejection of a pulse flow means an ejection in the state where the flow rate or flow speed varies, and is not limited to repetition of ejection and stop of the fluid. That is, various other ejection forms are included, such as a form in which there is a complete interruption between ejections, or a form in which there is a low-pressure flow between ejections.

Figure 2B:
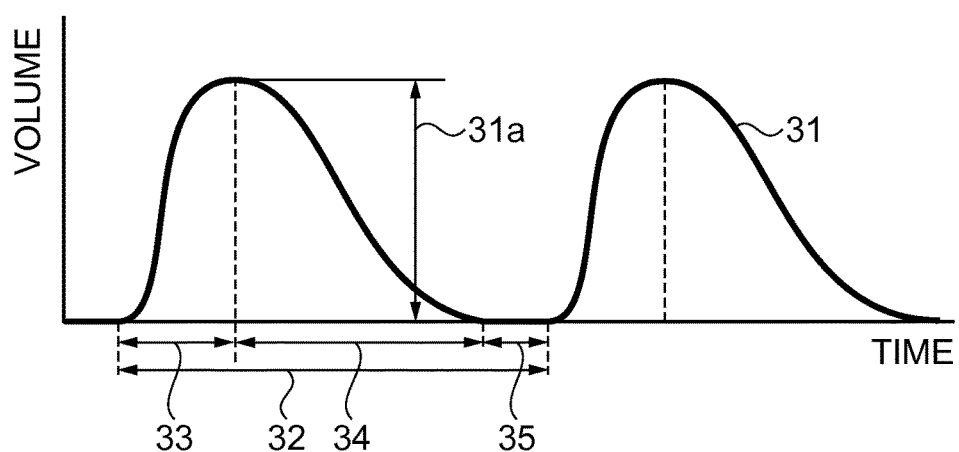
FIG. 2B is a graph showing transition of the volume of a liquid chamber.

FIG. 2B is a graph showing the transition of the volume in the liquid chamber. In FIG. 2B, the vertical axis represents the volume of the liquid chamber 22. The volume decreases as it goes up in the graph. The horizontal axis represents the transition of time. Time shifts from the left to the right in the graph. A volume transition line 31 shows the volume of liquid chamber 22 that is changed.

The volume transition line 31 is repeated on a cycle 32. One cycle 32 is divided into a rise section 33, a fall section 34, and a pause section 35. In the rise section 33, the volume transition line 31 has a shape similar to a sine waveform. At this time, a voltage is applied to the piezoelectric element 28 and the piezoelectric element 28 expands. Thus, the diaphragm 25 moves in the first direction 29 and the volume of the liquid chamber 22 decreases. Then, the liquid 12 in the liquid chamber 22 moves to the outlet channel 23.

In the fall section 34, the volume transition line 31 has a shape similar to a sine waveform. At this time, the voltage applied to the piezoelectric element 28 falls and the piezoelectric element 28 contracts. Thus, the diaphragm 25 moves in the second direction 30 and the volume of the liquid chamber 22 increases. Then, the liquid 12 flows into the liquid chamber 22 from the inlet channel 21. The fall section 34 is a longer time than the rise section 33. Thus, the liquid 12 flows out into the outlet channel 23 with great strength and flows in from the inlet channel 21 at a low speed. The pause section 35 is a section where the piezoelectric element 28 is maintained in the contracted state. Changing the length of the pause section 35 enables adjustment of the cycle 32.

The amount of change in the volume on the volume transition line 31 is defined as a volume change amount 31a. The volume change amount 31a can be adjusted as the control device 13 controls the piezoelectric element 28. In this manner, a pulse flow is formed in the pulsation applying part 5.

Figure 3:
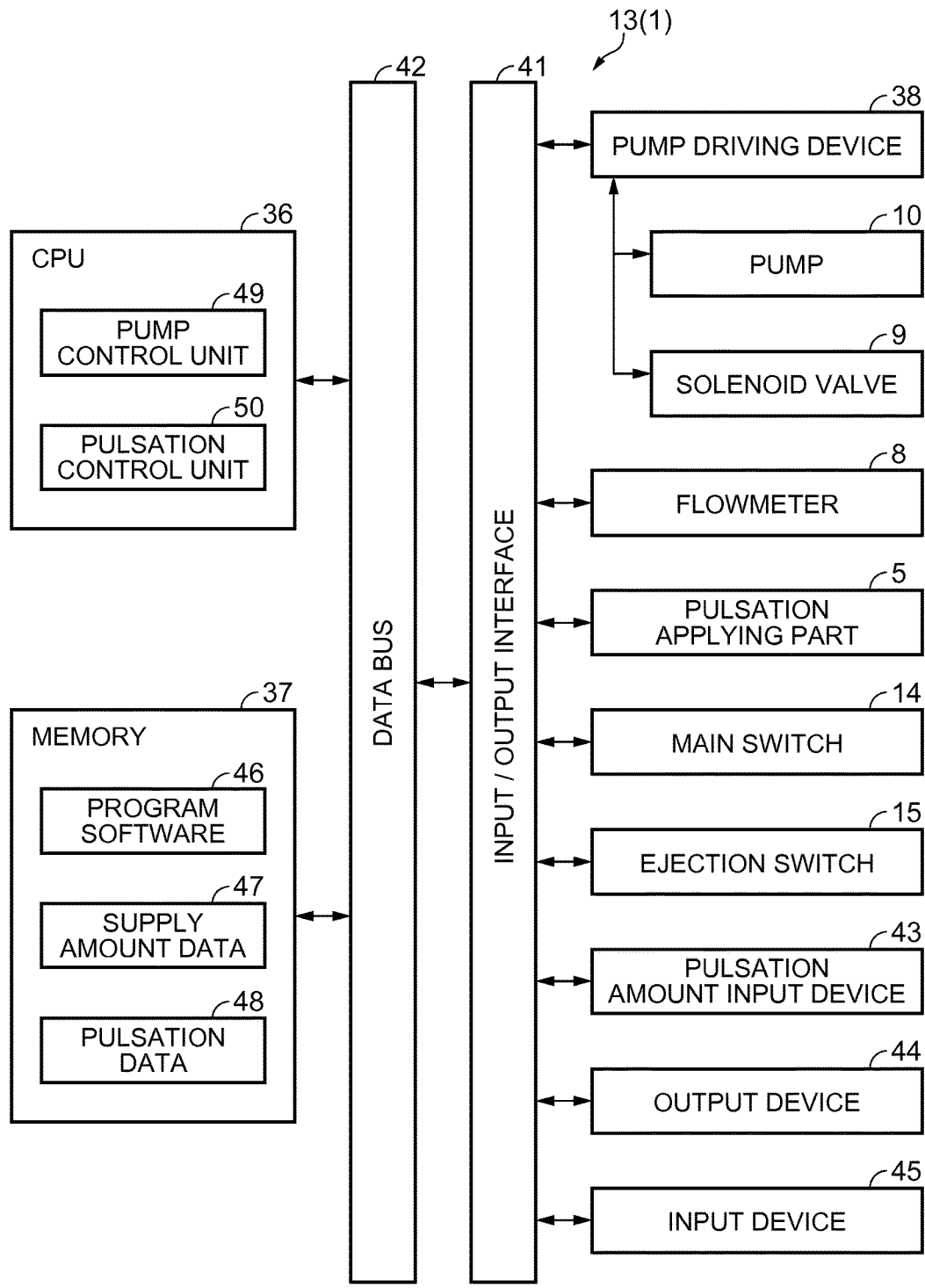
FIG. 3 is a block diagram showing the electric control of the liquid ejection device.

FIG. 3 is a block diagram showing the electric control of the liquid ejection device 1. In FIG. 3, the liquid ejection device 1 has the control device 13 for controlling the operations of the liquid ejection device 1. The control device 13 has a CPU 36 (central processing unit) which carries out various kinds of arithmetic processing as a processor, and a memory 37 which stores various kinds of information. A pump driving device 38, the flowmeter 8 and the pulsation applying part 5 are connected with the CPU 36 via an input/output interface 41 and a data bus 42. Moreover, the main switch 14, the ejection switch 15, a pulsation amount input device 43, an output device 44 and an input device 45 are connected with the CPU 36 via the input/output interface 41 and the data bus 42.

The pump driving device 38 is a device which drives the pump 10 and the solenoid valve 9. The pump driving device 38 takes in an instruction signal from the CPU 36. The pump driving device 38 then drives the pump 10 with the pressure or flow rate indicated by the instruction signal. The pump driving device 38 also drives the solenoid valve 9 to open and close the valve.

The main switch 14 is a switch for starting up the liquid ejection device 1. As the main switch 14 is turned on, the pump 10 is started up. Then, as the surgical operator turns on the ejection switch 15, the solenoid valve 9 opens and the liquid 12 is ejected from the nozzle 4.

The pulsation amount input device 43 is a device with which the surgical operator inputs the amount of variance in the pulsation of the liquid 12. The pulsation amount input device 43 is, for example, a device for setting the volume change amount 31a of the liquid chamber 22. The pulsation amount input device 43 can be formed, for example, by a variable resistor, a circuit or the like for converting a resistance value of the variable resistor, and a plurality of switches or the like.

The output device 44 may include a liquid crystal display device, a light or speaker for giving a notification of abnormality, a device which carries out wired and wireless communication with an external computer, or the like. Thus, the control device 13 can display and output the state of the liquid ejection device 1 and the setting state set by the surgical operator.

The input device 45 may include a keyboard or mouse-type input device, a pen-type input device, and a device which carries out wired and wireless communication with an external computer. By such an input device 45, various data are inputted to the memory 37.

The memory 37 is a concept including a semiconductor memory such as RAM and ROM, and an external storage device such as hard disk and DVD-ROM. Functionally, a storage area for storing program software 46 describing procedures for controlling the operations of the liquid ejection device 1, and a storage area for storing supply amount data 47 that is data used when calculating the amount of the liquid 12 supplied, are set. In addition, a storage area for storing pulsation data 48 that is data about the pulsation of the liquid 12 is set. Moreover, a storage area that functions as a work area, temporary file or the like for the CPU 36, and various other storage areas are set.

The CPU 36 is configured to perform control to eject the liquid 12 from the nozzle 4 of the handpiece 2 according to the program software 46 stored in the memory 37. The CPU has a pump control unit 49 as a specific function implementation unit. The pump control unit 49 outputs an instruction signal to the pump driving device 38 and thus performs control to drive the pump 10 and cause the liquid 12 to flow. The pump control unit 49 takes in the flow rate of the liquid 12 detected by the flowmeter 8, and controls the flow rate of the liquid 12 to be ejected. The pump control unit 49 also opens and closes the solenoid valve 9 and thus controls the liquid 12 to flow and stop flowing.

The CPU 36 also has a pulsation control unit 50. The pulsation control unit 50 takes in the pulsation data 48 set by the pulsation amount input device 43, from the memory 37. The pulsation control unit 50 controls the piezoelectric element 28 of the pulsation applying part 5 and thereby controls the volume change amount 31a of the liquid chamber 22. As the liquid chamber 22 changes, the liquid 12 is ejected in the form of a pulse flow.

In this embodiment, each of the functions is realized by the program software, using the CPU 36. However, if each function can be realized by a standalone electronic circuit (hardware) without using the CPU 36, such an electronic circuit can be used.

Next, a dissection method for dissecting the cellular tissue 16 using the liquid ejection device 1 will be described with reference to FIGS. 4A to 4D and FIGS. 5A to 5D. FIGS. 4A to 4D and FIGS. 5A to 5D are schematic views for explaining the dissection method for dissecting the cellular tissue. The site and type of the cellular tissue 16 are not particularly limited. However, here, for example, an example of splitting the median sulcus in order to extirpate a tumor in a vertebra is described. In the dissection of the median sulcus in the vertebra or the like, it is necessary not to cause unwanted damage to normal tissues of important blood vessels, nerves and the like. There is a high risk of damaging normal tissues where the tissues are bonded together firmly at the boundary of the tissues.

Figure 4A:
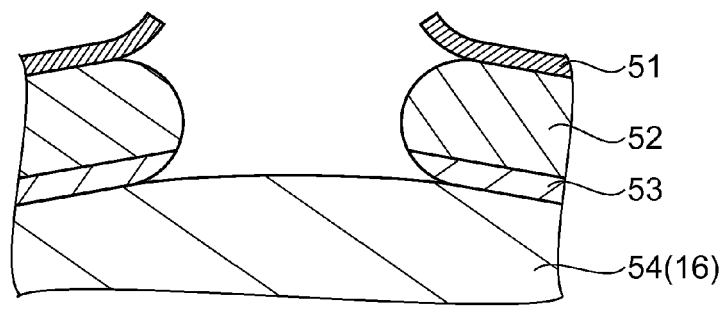
FIGS. 4A to 4D are schematic views for explaining a dissection method for dissecting a cellular tissue.
Figure 4B:
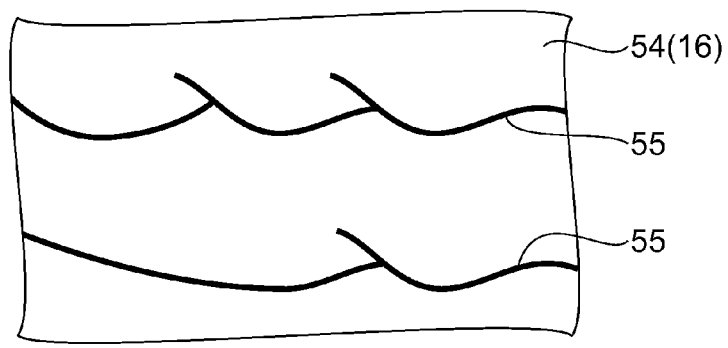

FIGS. 4A and 4B show the step of exposing a dissection site. As shown in FIG. 4A, the surgical operator removes a part of a skin tissue 51 and a part of a vertebra 52. The surgical operator also strips off a part of a dura mater 53 so as to expose the surface of a spinal cord 54. The spinal cord 54 is the cellular tissue 16 that is a target of dissection. As shown in FIG. 4B, blood vessels 55 extend through the spinal cord 54.

Figure 4C:
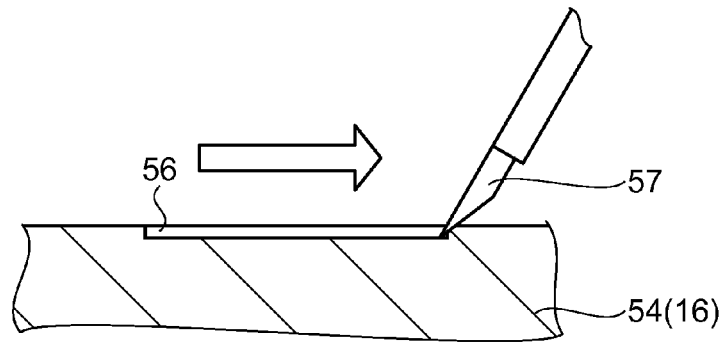
Figure 4D:
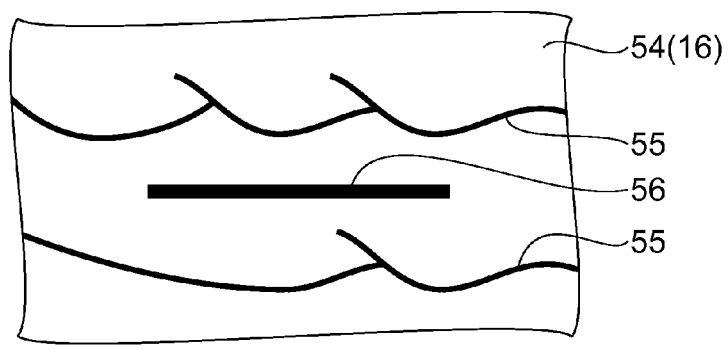

FIGS. 4C and 4D show the step of forming an incision at the dissection site. As shown in FIG. 4C, an incision 56 is formed at the site where the cellular tissue 16 of the spinal cord 54 is to be dissected. The incision 56 is formed shallowly with a metallic surgical knife 57 along the site where tissues are to be split. Consequently, the incision 56 is arranged on the surface of the spinal cord 54, as shown in FIG. 4D.

Figure 5A:
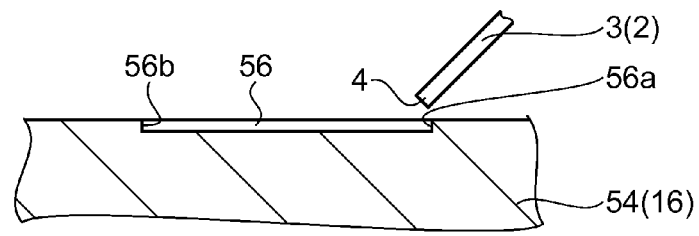
FIGS. 5A to 5D are schematic views for explaining a dissection method for dissecting a cellular tissue.

FIG. 5A shows a step of installing the nozzle 4 at the position of the incision 56. As shown in FIG. 5A, the incision 56 extends from a first end 56a to a second end 56b. The surgical operator arranges the nozzle 4 in such a way as to face the first end 56a. The handpiece 2 is installed in such a way that the ejection tube 3 is oblique to the tangential direction to the surface of the lump of the cellular tissue 16. The liquid 12 is ejected along the direction in which the ejection tube 3 extends. Therefore, the liquid 12 is ejected obliquely to the tangential direction to the surface of the cellular tissue 16. The ejection tube 3 is installed in such a way that the nozzle 4 faces toward the second end 56b.

Figure 5B:
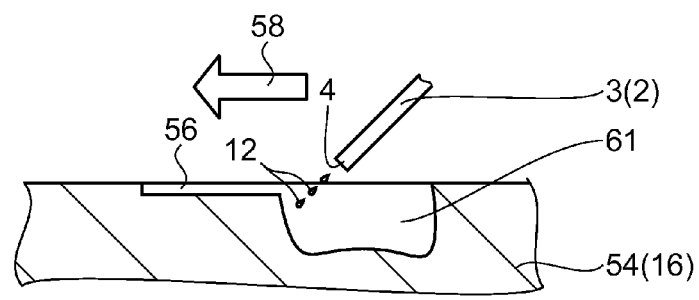
Figure 5C:
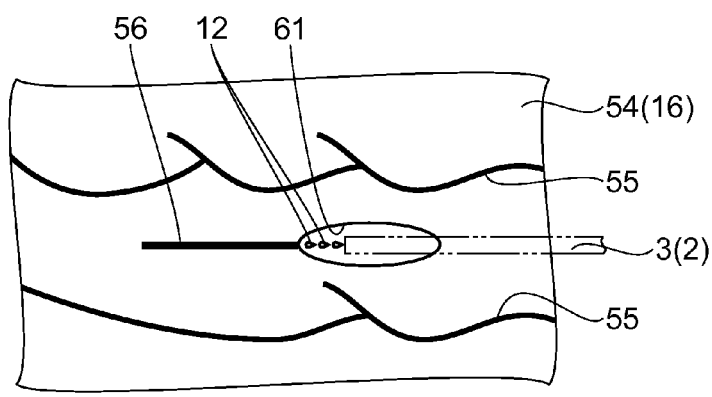
Figure 5D:
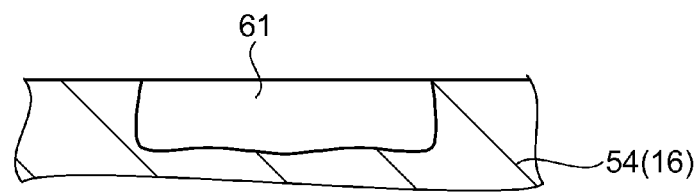

FIGS. 5B to 5D show the step of ejecting the liquid 12 to the incision 56 from the nozzle 4. As shown in FIGS. 5B and 5C, the surgical operator causes the liquid 12 to be ejected toward the incision 56 from the nozzle 4. Then, the surgical operator moves the handpiece 2 from the first end 56a toward the second end 56b. The liquid 12 is ejected to the incision 56 so as to expand the incision 56, and the cellular tissue 16 is thus dissected. The cellular tissue 16 is dissected with the water pressure of the ejected liquid 12. When the liquid 12 is ejected to the incision 56, stress concentrates at the end of the incision 56. Therefore, the cellular tissue 16 can be dissected even when the water pressure is low.

If there is no incision 56, an extremely high water pressure is needed. In this case, the water pressure at the time of dissecting the surface of the cellular tissue 16 reaches the inside of the cellular tissue 16. Since the extremely high water pressure is applied to the inside of the cellular tissue 16, it is difficult to control the depth to which the cellular tissue 16 is dissected. Meanwhile, if the incision 56 is formed, dissection along the incision can be achieved with a low water pressure. Therefore, the depth and direction in which the cellular tissue 16 is dissected can be easily controlled.

The liquid 12 is ejected in the form of a pulse flow. Using the pulse flow enables increase in the pressure fluctuation applied to the cellular tissue 16. As the pressure fluctuation increases, fatigue fracture can occur more easily in the part that connects cells together. Therefore, this part can be easily cut.

The liquid 12 is ejected in such a way as to advance obliquely to the tangential direction to the surface of the cellular tissue 16. Then, the site to which the liquid 12 is applied is moved in a direction in which the angle formed by the surface of the cellular tissue 16 and the direction of advancement of the liquid 12 is greater. The liquid 12 accumulates in the incision 56 at the site where the liquid is ejected. Then, the site where the liquid 12 is applied to the cellular tissue 16 is moved in an advancing direction 58. Therefore, the nozzle 4 is moved while ejecting the liquid 12, in such a way as to push the liquid 12 accumulating in the incision 56. Consequently, the liquid pushed by the water pressure heads in the direction of pushing and expanding the incision 56. Therefore, the incision 56 can be expanded easily.

At the site where the liquid 12 is ejected, the incision 56 is expanded to form a dissection part 61. As the surgical operator moves the handpiece 2 in the advancing direction 58, the incision 56 turns into the dissection part 61. Consequently, the entire incision 56 becomes the dissection part 61, as shown in FIG. 5D. Moreover, the liquid 12 may be ejected to the dissection part 61 so as to deepen or elongate the dissection part 61. The formation of the incision 56 and the formation of the dissection part 61 are repeated. The median sulcus of the spinal cord 54 is opened, and the tumor inside is extirpated. Then, the surgical operation ends.

As described above, the embodiment has the following advantageous effects.

(1) According to the embodiment, the incision 56 is formed at the site where the cellular tissue 16 is to be dissected. Then, the liquid 12 is ejected to the incision 56 so as to expand the incision 56. When the liquid 12 is ejected to the incision 56, stress concentrates at the end of the incision 56. Therefore, the cellular tissue 16 can be dissected along the incision even when the water pressure is low. Since the water pressure is low, the depth and direction in which the cellular tissue 16 is dissected can be controlled easily.

(2) According to the embodiment, the liquid 12 is ejected in the form of a pulse flow. Using the pulse flow enables increase in the pressure fluctuation applied to the cellular tissue 16. As the pressure fluctuation increases, fatigue fracture can occur more easily in the part that connects cells together. Therefore, the cellular tissue 16 can be dissected easily.

(3) According to the embodiment, the liquid 12 is ejected in such a way as to advance obliquely to the tangential direction to the surface of the cellular tissue 16. The liquid 12 accumulates in the incision 56 at the site where the liquid is ejected. Then, the nozzle 4 is moved in the direction in which the angle formed by the surface and the direction of advancement of the liquid 12 is greater. Therefore, the nozzle 4 is moved while ejecting the liquid 12, in such a way as to push the liquid 12 accumulating in the incision 56.

Consequently, the liquid 12 pushed by the water pressure heads in the direction of pushing and expanding the incision 56. Therefore, the incision 56 can be expanded easily.

Second Embodiment

Figure 6:
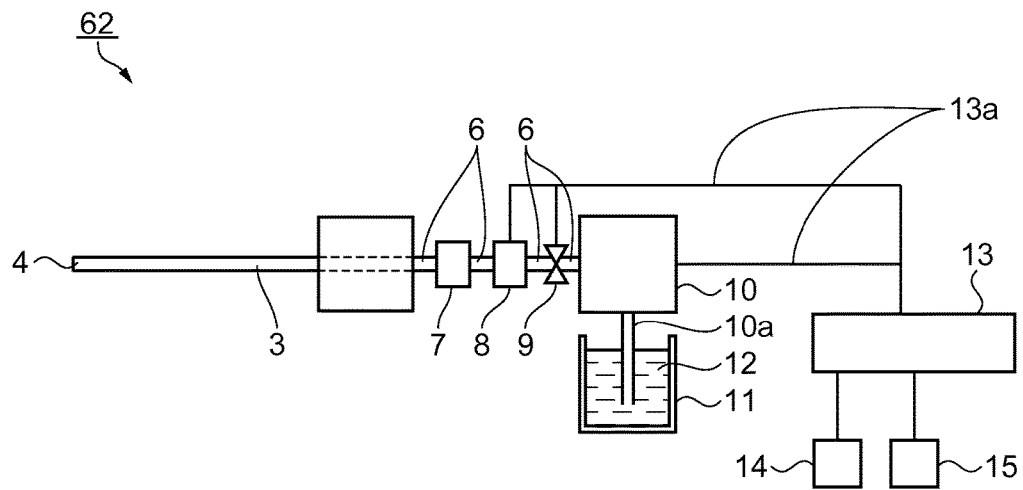
FIG. 6 is a block diagram showing the configuration of a liquid ejection device according to a second embodiment.

Next, an embodiment of a liquid ejection device will be described with reference to the block diagram of FIG. 6 showing the configuration of the liquid ejection device.

This embodiment is different from the first embodiment in that the pulsation applying part 5 of FIG. 1A is eliminated. The same features as in the first embodiment will not be described further.

That is, in this embodiment, in a liquid ejection device 62, the tube 6 is connected with the ejection tube 3, as shown in FIG. 6. As the surgical operator turns on the ejection switch 15, the liquid 12 is continuously ejected from the nozzle 4. Again, when the cellular tissue 16 can be dissected, a configuration without the pulsation applying part 5 may be employed. Since the pulsation applying part 5 and the pulsation control unit 50 can be omitted, the liquid ejection device 62 that can be easily manufactured is provided.

Third Embodiment

Figure 7:
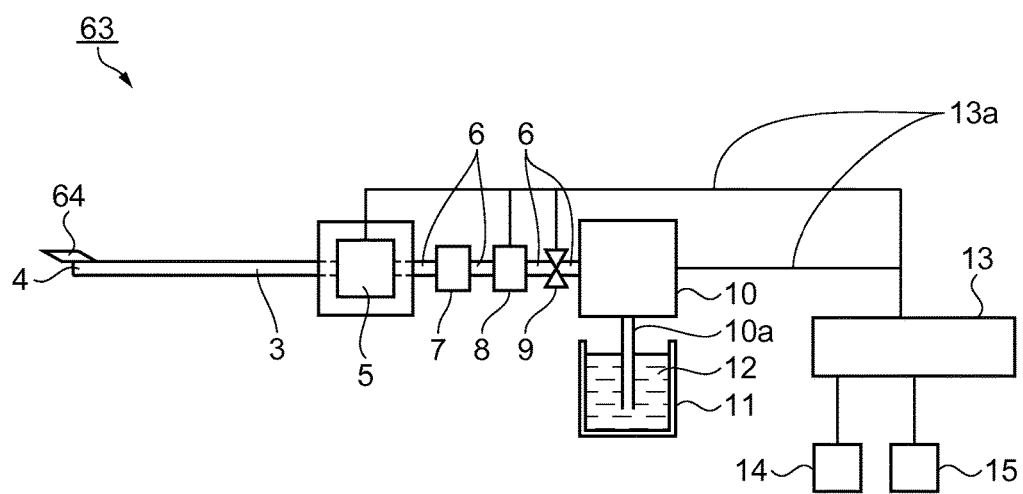
FIG. 7 is a block diagram showing the configuration of a liquid ejection device according to a third embodiment.

Next, an embodiment of a liquid ejection device will be described with reference to the block diagram of FIG. 7 showing the configuration of the liquid ejection device.

This embodiment is different from the first embodiment in that an edge portion 64 is installed near the nozzle 4. The same features as in the first embodiment will not be described further.

That is, in this embodiment, in a liquid ejection device 63, the edge portion 64 is installed on the ejection tube 3, as shown in FIG. 7. Thus, the surgical operator can form the incision 56 on the surface of the cellular tissue 16 and eject the liquid 12 toward the incision 56 from the nozzle 4. Since the liquid ejection device 63 has the edge portion 64, the surgical operator can carry out both the formation of the incision 56 and the ejection of the liquid 12, using the liquid ejection device 63. Therefore, since the surgical operator need not hold a plurality of tools one after another, the cellular tissue 16 can be dissected with high operability.

The edge portion 64 is installed side by side with the nozzle 4. The end of the edge portion 64 is installed, protruding ahead of the end of the nozzle 4 in the direction in which the liquid 12 is ejected. Thus, the surgical operator can carry out the formation of the incision 56 and the ejection of the liquid 12 without changing the way of holding the liquid ejection device 63.

It should be noted that the embodiments are not limited to the above embodiments and that a person with ordinary skills in the art can make various changes and improvements without departing from the technical scope of the invention. Modifications will be described below.

Modification 1

In the first embodiment, an example of dissecting the cellular tissue 16 of the spinal cord 54 is described. However, the application is not limited to the spinal cord 54 and a similar method to this embodiment may be used when dissecting the cellular tissue 16 at another site. The subject to be treated may be limited to animals excluding humans. Also, the cellular tissue 16 is not limited to a living body and may be a part of a corpse. In such cases, too, since the cellular tissue 16 can be dissected along the incision with a low water pressure, the depth and direction in which the cellular tissue is dissected can be controlled easily.

Modification 2

In the first embodiment, an example of splitting the median sulcus of the spinal cord 54 is described. However, a similar method to this embodiment may also be used in an interhemispheric approach. Also, a similar method to this embodiment may be used in various surgical methods for separation of a tumor from normal tissues, separation of a blood vessel from tissues, and the like. In such cases, too, since the cellular tissue 16 can be dissected along the incision with a low water pressure, the depth and direction in which the cellular tissue is dissected can be controlled easily.

What is claimed is:

1. A cellular tissue dissection method comprising:
    forming an incision at a site where a cellular tissue is to be dissected; wherein the incision is formed by a knife that is different than a dissecting device used to eject the liquid into the incision for dissecting the cellular tissue; and
    ejecting a liquid to the incision, expanding the incision, and dissecting the cellular tissue.

2. The cellular tissue dissection method according to claim 1, wherein
the liquid is ejected in the form of a pulse flow.

3. The cellular tissue dissection method according to claim 1, wherein
the liquid is ejected in such a way as to advance obliquely to a tangential direction to a surface of the cellular tissue, and
a site where the liquid is applied to the surface is moved in a direction in which an angle formed by the tangential direction to the surface and the direction of advancement of the liquid is greater.

* * * * *